(12) United States Patent
Imran et al.

(10) Patent No.: US 7,689,284 B2
(45) Date of Patent: Mar. 30, 2010

(54) PSEUDOUNIPOLAR LEAD FOR STIMULATING A DIGESTIVE ORGAN

(75) Inventors: Mir A. Imran, Los Altos Hills, CA (US); Jacob Anthiah Bashyam, Santa Clara, CA (US)

(73) Assignee: IntraPace, Inc., Menlo Park, CA (US)

( * ) Notice: Subject to any disclaimer, the term of this patent is extended or adjusted under 35 U.S.C. 154(b) by 604 days.

(21) Appl. No.: 11/249,290

(22) Filed: Oct. 12, 2005

(65) Prior Publication Data

US 2006/0074457 A1 Apr. 6, 2006

Related U.S. Application Data

(60) Continuation of application No. 10/295,128, filed on Nov. 14, 2002, which is a division of application No. 09/847,884, filed on May 1, 2001, now Pat. No. 6,535,764, and a continuation of application No. 11/219,004, filed on Sep. 1, 2005.

(51) Int. Cl.
*A61N 1/18* (2006.01)
*A61N 1/04* (2006.01)

(52) U.S. Cl. .................. 607/40; 607/126; 607/133; 607/73

(58) Field of Classification Search .......... 607/40, 607/73, 126, 130, 133
See application file for complete search history.

(56) References Cited

U.S. PATENT DOCUMENTS

| | | | |
|---|---|---|---|
| 3,411,507 A | 11/1968 | Wingrove | 128/422 |
| 3,646,940 A | 3/1972 | Timm, et al. | 128/421 |
| 3,662,758 A | 5/1972 | Glover | 128/419 |
| 3,677,251 A | 7/1972 | Bowers | 128/419 |
| 3,735,766 A | 5/1973 | Bowers, et al. | 128/419 |
| 3,796,221 A | 3/1974 | Hagfors | 128/421 |
| 3,815,611 A | 6/1974 | Denniston, III | 128/419 |
| 3,835,865 A | 9/1974 | Bowers | 128/419 |
| 4,102,344 A | 7/1978 | Conway et al. | 128/419 |
| 4,135,518 A * | 1/1979 | Dutcher | 600/374 |
| 4,153,059 A | 5/1979 | Fravel et al. | |
| RE30,366 E | 8/1980 | Rasor et al. | 128/419 |
| 4,338,945 A | 7/1982 | Kosugi et al. | |
| 4,431,000 A | 2/1984 | Butler et al. | |
| 4,571,556 A | 2/1986 | Gnerlich et al. | |

(Continued)

FOREIGN PATENT DOCUMENTS

EP 0129483 12/1984

(Continued)

OTHER PUBLICATIONS

C. Paul Swain, et al., an Endoscopically Deliverable Tissue-Transfixing Device for Securing Biosensors in the Gastrointestinal Tract, Gastrointestinal Endoscopy, 40/6:730-734 (1994).

(Continued)

*Primary Examiner*—Carl H Layno
*Assistant Examiner*—Natasha N Patel
(74) *Attorney, Agent, or Firm*—Townsend and Townsend and Crew LLP

(57) ABSTRACT

A pseudounipolar stimulator lead for anchoring to a digestive organ is provided.

16 Claims, 3 Drawing Sheets

U.S. PATENT DOCUMENTS

| | | | |
|---|---|---|---|
| 4,628,928 A | 12/1986 | Lowell | 128/303 |
| 4,690,145 A | 9/1987 | King-Smith et al. | |
| 4,699,143 A | 10/1987 | Dufresne et al. | |
| 4,823,808 A | 4/1989 | Clegg et al. | 128/773 |
| 4,921,481 A | 5/1990 | Danis et al. | 604/67 |
| 4,925,446 A | 5/1990 | Garay et al. | 604/96 |
| 5,188,104 A | 2/1993 | Wernicke et al. | 128/419 |
| 5,197,491 A | 3/1993 | Anderson et al. | 128/786 |
| 5,217,449 A | 6/1993 | Yuda et al. | 604/890 |
| 5,292,344 A | 3/1994 | Douglas | 607/40 |
| 5,411,527 A * | 5/1995 | Alt | 607/5 |
| 5,415,181 A | 5/1995 | Hogrefe et al. | 128/736 |
| 5,423,872 A | 6/1995 | Cigaina | 607/40 |
| 5,540,730 A | 7/1996 | Terry, Jr. et al. | 607/40 |
| 5,558,640 A | 9/1996 | Pfeiler et al. | 604/67 |
| 5,690,691 A | 11/1997 | Chen et al. | 607/40 |
| 5,716,392 A | 2/1998 | Bourgeois et al. | 607/132 |
| 5,792,048 A | 8/1998 | Schaefer | 600/302 |
| 5,800,445 A | 9/1998 | Ratcliff et al. | 606/116 |
| 5,836,994 A | 11/1998 | Bourgeois | 7/40 |
| 5,861,014 A | 1/1999 | Familoni | 607/40 |
| 5,928,195 A | 7/1999 | Malamud et al. | 604/141 |
| 5,993,473 A | 11/1999 | Chan et al. | 606/192 |
| 5,995,872 A | 11/1999 | Bourgeois | 7/40 |
| 6,004,319 A * | 12/1999 | Goble et al. | 606/48 |
| 6,026,326 A | 2/2000 | Bardy | 607/40 |
| 6,041,258 A | 3/2000 | Cigaina et al. | 607/40 |
| 6,083,249 A | 7/2000 | Familoni | 607/40 |
| 6,091,992 A | 7/2000 | Bourgeois et al. | 607/40 |
| 6,097,984 A | 8/2000 | Douglas | 607/40 |
| 6,098,629 A | 8/2000 | Johnson et al. | 128/897 |
| 6,104,955 A | 8/2000 | Bourgeois | 7/40 |
| 6,115,635 A | 9/2000 | Bourgeois | 7/40 |
| 6,205,359 B1 | 3/2001 | Boveja | 607/45 |
| 6,216,039 B1 | 4/2001 | Bourgeois | 7/40 |
| 6,243,607 B1 | 6/2001 | Mintchev et al. | 607/40 |
| 6,285,897 B1 | 9/2001 | Kilcoyne et al. | |
| 6,321,124 B1 | 11/2001 | Cigaina | 607/133 |
| 6,327,503 B1 | 12/2001 | Familoni | 607/40 |
| 6,366,814 B1 | 4/2002 | Boveja et al. | 607/45 |
| 6,381,495 B1 | 4/2002 | Jenkins | 607/40 |
| 6,427,089 B1 | 7/2002 | Knowlton | |
| 6,449,511 B1 | 9/2002 | Mintchev et al. | 607/40 |
| 6,453,199 B1 | 9/2002 | Kobozev | 607/40 |
| 6,454,785 B2 | 9/2002 | De Hoyos Garza | |
| 6,477,423 B1 | 11/2002 | Jenkins | 607/40 |
| 6,510,332 B1 | 1/2003 | Greenstein | 600/377 |
| 6,529,778 B2 | 3/2003 | Prutchi | 607/119 |
| 6,540,789 B1 | 4/2003 | Silverman et al. | 623/23.65 |
| 6,542,776 B1 | 4/2003 | Gordon et al. | 607/40 |
| 6,564,101 B1 | 5/2003 | Zikria | 607/40 |
| 6,571,127 B1 | 5/2003 | Ben-Haim et al. | 607/40 |
| 6,591,137 B1 | 7/2003 | Fischell et al. | 607/40 |
| 6,600,953 B2 | 7/2003 | Flesler et al. | 607/40 |
| 6,606,518 B1 | 8/2003 | Cigaina | 607/41 |
| 6,606,523 B1 | 8/2003 | Jenkins | 607/133 |
| 6,609,025 B2 | 8/2003 | Barrett et al. | 607/2 |
| 6,611,715 B1 | 8/2003 | Boveja | 607/40 |
| 6,615,084 B1 | 9/2003 | Cigaina | 607/40 |
| 6,684,104 B2 | 1/2004 | Gordon et al. | 607/40 |
| 6,826,428 B1 | 11/2004 | Chen et al. | 607/40 |
| 6,879,859 B1 | 4/2005 | Boveja | 607/45 |
| 6,895,278 B1 | 5/2005 | Gordon | 607/40 |
| 6,895,279 B2 | 5/2005 | Loeb et al. | 607/40 |
| 6,999,819 B2 * | 2/2006 | Swoyer et al. | 607/117 |
| 7,020,526 B1 | 3/2006 | Zhao | |
| 7,054,692 B1 | 5/2006 | Whitehurst et al. | |
| 2002/0072780 A1 | 6/2002 | Foley | 607/40 |
| 2002/0103424 A1 | 8/2002 | Swoyer et al. | 600/350 |
| 2002/0103521 A1 | 8/2002 | Swoyer et al. | 607/116 |
| 2002/0103522 A1 | 8/2002 | Swoyer et al. | 607/116 |
| 2002/0161414 A1 | 10/2002 | Flesler et al. | 607/40 |
| 2002/0198570 A1 | 12/2002 | Puskas | 607/2 |
| 2002/0198571 A1 | 12/2002 | Puskas | 604/2 |
| 2003/0055463 A1 | 3/2003 | Gordon et al. | 607/40 |
| 2003/0120328 A1 | 6/2003 | Jenkins et al. | 607/2 |
| 2003/0144708 A1 | 7/2003 | Starkebaum | 607/116 |
| 2003/0195600 A1 | 10/2003 | Tronnes et al. | 607/133 |
| 2003/0212439 A1 | 11/2003 | Schuler et al. | 607/40 |
| 2004/0015201 A1 | 1/2004 | Greenstein | 607/40 |
| 2004/0059393 A1 | 3/2004 | Policker et al. | 607/40 |
| 2004/0088022 A1 | 5/2004 | Chen | 607/40 |
| 2004/0093039 A1 | 5/2004 | Schumert | 607/40 |
| 2004/0133089 A1 | 7/2004 | Kilcoyne et al. | 600/350 |
| 2004/0147816 A1 | 7/2004 | Policker et al. | 600/300 |
| 2004/0162595 A1 | 8/2004 | Foley | 607/40 |
| 2004/0167583 A1 | 8/2004 | Knudson et al. | 607/40 |
| 2004/0172084 A1 | 9/2004 | Knudson et al. | 607/40 |
| 2004/0172085 A1 | 9/2004 | Knudson et al. | 607/40 |
| 2004/0172086 A1 | 9/2004 | Knudson et al. | 607/40 |
| 2004/0172088 A1 | 9/2004 | Knudson et al. | 607/40 |
| 2004/0172095 A1 | 9/2004 | Jenkins et al. | 607/116 |
| 2004/0176812 A1 | 9/2004 | Knudson et al. | 607/40 |
| 2004/0236381 A1 | 11/2004 | Dinsmoor et al. | 607/40 |
| 2004/0236382 A1 | 11/2004 | Dinsmoor et al. | 607/40 |
| 2005/0021101 A1 | 1/2005 | Chen et al. | 607/40 |
| 2005/0038454 A1 | 2/2005 | Loshakove et al. | 606/153 |
| 2005/0049655 A1 | 3/2005 | Boveja et al. | 607/58 |
| 2005/0055039 A1 | 3/2005 | Burnett et al. | |
| 2005/0065575 A1 | 3/2005 | Dobak | |
| 2005/0096514 A1 | 5/2005 | Starkebaum | |
| 2005/0113880 A1 | 5/2005 | Gordon | 436/106 |
| 2005/0131485 A1 | 6/2005 | Knudson et al. | 607/40 |
| 2005/0131486 A1 | 6/2005 | Boveja et al. | |
| 2005/0131487 A1 | 6/2005 | Boveja et al. | |
| 2005/0137643 A1 | 6/2005 | Mintchev | |
| 2005/0137644 A1 | 6/2005 | Boveja et al. | |
| 2005/0149141 A1 | 7/2005 | Starkebaum | 607/40 |
| 2005/0149142 A1 | 7/2005 | Starkebaum | 607/40 |
| 2005/0149146 A1 | 7/2005 | Boveja et al. | |
| 2005/0159800 A1 | 7/2005 | Marshall et al. | 607/122 |
| 2005/0159801 A1 | 7/2005 | Marshall et al. | 607/122 |
| 2005/0222637 A1 | 10/2005 | Chen | |
| 2005/0222638 A1 | 10/2005 | Foley et al. | 607/40 |
| 2005/0251219 A1 | 11/2005 | Evans | |
| 2006/0020298 A1 | 1/2006 | Camilleri et al. | |
| 2006/0025654 A1 | 2/2006 | Suzuki et al. | |
| 2006/0036293 A1 | 2/2006 | Whitehurst et al. | |
| 2006/0058851 A1 | 3/2006 | Cigaina | |
| 2006/0074335 A1 | 4/2006 | Ben-Oren et al. | |
| 2006/0074450 A1 | 4/2006 | Boveja et al. | |
| 2006/0074458 A1 | 4/2006 | Imran | |
| 2006/0085054 A1 | 4/2006 | Zikorus et al. | |
| 2006/0089571 A1 | 4/2006 | Gertner | |
| 2006/0089690 A1 | 4/2006 | Gerber | |
| 2006/0089699 A1 | 4/2006 | Imran | |
| 2006/0095078 A1 | 4/2006 | Tronnes | |
| 2006/0116736 A1 | 6/2006 | DiLorenzo | |
| 2007/0049986 A1 | 3/2007 | Imran | |
| 2008/0051850 A1 | 2/2008 | Sparks et al. | |

FOREIGN PATENT DOCUMENTS

| | | |
|---|---|---|
| EP | 0571938 | 12/1993 |
| WO | WO 9843700 | 8/1998 |
| WO | 9853878 | 12/1998 |
| WO | WO 0030534 | 6/2000 |
| WO | 0176690 | 1/2001 |
| WO | 0158389 | 8/2001 |
| WO | WO 0176690 | 10/2001 |

| | | |
|---|---|---|
| WO | WO 0226101 | 4/2002 |

OTHER PUBLICATIONS

Keith E. Kelly, et al., Pacing the Canine Stomach With Electric Stimulation, *Am. J. Of Physiology*, 222/3:588-594 (Mar. 1972).

J. Chris Eagon et al., Gastrointestinal Pacing, *Surgical Clinics of North America*, 73/6:1161-1172 (Dec. 1993).

Valerio Cigaina, et al., Gastric Myo-Electrical Pacing As Therapy for Morbid Obesity: Preliminary Results.

H. Geldof, et al., Electrogastrographic Study of Gastric Myoelectrical Activity in Patients With Unexplained Nausea and Vomiting, Gut, 27:799-808, (1986).

Brent W. Miedema, et al., Pacing the Human Stomach, Surgery, 143-150, (Feb. 1992).

Keith A. Kelly, Differential Responses of the Canine Gastric Corpus and Antrum to Electric Stimulation, *Am. J. Of Physiology*, 226/1:230-234, (Jan. 1974).

Electric Stimulation of the Gastrointestinal Tract, GP, p. 151 (Apr. 1964).

Michael P. Hocking, Postoperative Gastroparesis and Tachygastria-Response to Electric Stimulation and Erythromycin, *Surgery*, 114/3:538-542 (Sep. 1993).

Keith A. Kelly et al., Role of the Gastric Pacesetter Potential Defined by Electrical Pacing, *Canadian J. Of Physiology and Pharmacology*, 50:1017-1019, (1972).

Babajide O. Familoni, Efficacy of Electrical Stimulation at Frequencies Higher Than Basal Rate in Canine Stomach, *Digestive Diseases and Sciences*, 42/5:892-897, (May 1997).

Bader-Eddine Bellahsene, et al., Evaluation of a Portable Gastric Stimulator, Ninth Annual Conference of the Engineering in Medicine and Biology Society, (1987).

J. Chris Eagon, et al., Effects of Gastric Pacing on Canine Gastric Motility and Emptying, *The American Physiological Society*, 265/4:G767-G774, (Oct. 1993).

Babajide O. Familoni, et al., Electrical Pacing of the Stomach in Dogs.

S. K. Sarna, et al., Electrical Stimulation of Gastric Electrical Control Activity, *Am. J. Of Physiology*, 225/1:125-131, (Jul. 1973).

S. K. Sarna, et al., Gastric Pacemakers, *Gastroenterology*, 70:226-231, (1976).

Edwin E. Daniel, et al., Electrical Activity of the Gastrointestinal Tract as an Indication of Mechanical Activity, *Am. J. of Digestive Diseases*, 8/1:54-102, (1963).

M. Kubota, ert al., Manometric Evaluation of Children With Chronic Constipation Using a Suction-Stimulating Electrode, *Eu. J. Pediari. Surg.*, 2:287-290, (1992).

\* cited by examiner

PSEUDOUNIPOLAR LEAD FOR STIMULATING A DIGESTIVE ORGAN

RELATED APPLICATION DATA

This application is a continuation-in-part of U.S. application Ser. No. 10/295,128, filed Nov. 14, 2002 which is a divisional of U.S. application Ser. No. 09/847,884 now U.S. Pat. No. 6,535,764; and is also a continuation-in-part of U.S. application Ser. No. 11/219,004, filed Sep. 1, 2005.

FIELD OF THE INVENTION

This invention relates to an electrical lead or stimulator for attaching to the wall of a digestive organ.

BACKGROUND OF THE INVENTION

Digestive organ stimulation using electrodes coupled to the organ have been proposed in a variety of applications. Currently these devices are typically delivered to the organ by way of a laparoscopic surgical procedure, i.e., in which an incision is made in the stomach and the leads are tunneled through the abdominal tissue.

Copending parent application Ser. No. 10/295,128, filed Nov. 14, 2002 and its parent application Ser. No. 09/847,884 now U.S. Pat. No. 6,535,764 both of which are incorporated in their entirety herein by reference, describe an endoscopically delivered stimulation device that is attached to the inside of the stomach from within the stomach.

Generally bipolar or monopolar leads have been provided in the proposed devices. Monopolar stimulation may cause inadvertent stimulation of tissue adjacent the stimulating lead. Organs immediately adjacent the stomach may have an unintended physiological response to such stimulation.

Accordingly when stimulating the stomach or other digestive organs it may be desirable to concentrate stimulation to a small area. However, digestive organ walls are relatively thin (typically about 10 mm) so that placement of bipolar electrodes on or through the walls in a manner that maintains electrical contact may also cause shunting between the electrodes. Additionally, the mucosa of the stomach has a high impedance further reducing the effectiveness of bipolar electrodes stimulating through the mucosa.

SUMMARY OF THE INVENTION

In accordance with one variation of the invention an electrical stimulator is provided for stimulating a digestive organ where a stimulating electrode and a return electrode are a sufficient distance apart to reduce shunting. In accordance with another variation of the invention, a return electrode having a sufficiently large area and a sufficiently low impedance so that stimulation is effective when positioned adjacent higher impedance tissue such as the mucosa of the stomach. In accordance with another variation of the invention a stimulator is provided with electrodes that may be positioned in close enough proximity to avoid unwanted stimulation of adjacent tissue.

One aspect of the present invention provides a pseudounipolar stimulation device and method. Pseudounipolar electrodes in accordance with the invention are electrodes that comprise a stimulation electrode and a larger area return electrode that are used in a relatively close proximity, e.g. in near field stimulation. Accordingly, current flow can be limited to a desired region, while reducing shunting and resulting suboptimal energy consumption typical of bipolar electrode pairs in some tissue stimulation applications. Thus, pseudounipolar electrodes allow for improved control of current flow and energy consumption.

A variation of the invention provides a lead for stimulating a digestive organ. Another aspect of the invention provides a device and method for electrically stimulating a digestive organ. Electrical stimulation is generally defined herein to mean any application of an electrical signal or of an electromagnetic field to tissue of the digestive organ for a therapeutic purpose. While the device system and method may be used with any digestive tract organ and/or gastrointestinal tract organ, it is described with particular reference to use in a stomach.

In one variation, stimulation is applied to the stomach, for example, to treat digestive disorders or conditions, nausea, obesity or pain symptoms. The stimulation may affect the smooth muscle contractions and/or nerves associated with the stomach. Stimulation may also be used to affect motility. In one variation, the device is designed to facilitate or expedite mixing or breaking down of food matter or liquids in the stomach. In another variation, the device is designed to control, facilitate or expedite movement of food matter or liquids through the stomach and into the small intestine. In another variation, the device is designed to stimulate the stomach to delay passage of food from the stomach and into the small intestine.

The device of an embodiment of the present invention may reside in part or in whole within the patient's stomach. A device may include: a lead including at least one stimulating electrode in electrical contact with the stomach wall when implanted. It may also include an electronics unit containing the electronic circuitry of the device; or an attachment or coupling system for attaching or coupling a device or lead to the stomach.

The device of the present invention may be deployed from an abdominal approach (e.g., using open or laparoscopic surgery) or an endoscopic approach (through the esophagus), or a combination of approaches.

A device in accordance with one aspect of the invention includes: a first stimulating electrode in electrical contact with the stomach wall and having a first surface area, and a second return electrode within the vicinity of the first electrode and having a second surface area significantly larger than the surface area of the first electrode. The device may further comprise a retention device and/or anchor configured to couple the first electrode to the wall or tissue of the organ. The retention device or anchor may also couple the second electrode to the organ, or a second device may couple the second electrode to the organ in the vicinity of the first electrode. The device may further comprise an attachment device configured to attach the electronics housing to an organ wall. One or more of the first or second electrodes may also be located on an electronics unit housing coupled to the organ.

The device if used in the stomach comprises components are constructed of materials that allow it to withstand and function in the highly acidic environment of the stomach for two or more years.

In addition to the device being capable of stimulating the digestive organ, the electrodes of the device may also be used for diagnostic purposes. For example, the electrodes may be used to sense and observe electrical activity in the digestive organ. Such sensing may be used over time to identify patterns, diagnose diseases and evaluate effectiveness of various treatment protocols. For example irregular or lack of EGG (electrogastrogram) activity may be sensed. Stimulation may be provided in response to sensed EGG activity or lack of activity.

Various and further aspects of the invention are described in the following detailed description and claims.

DETAILED DESCRIPTION OF THE DRAWINGS

DETAILED DESCRIPTION OF THE PREFERRED EMBODIMENTS

Figure 1:
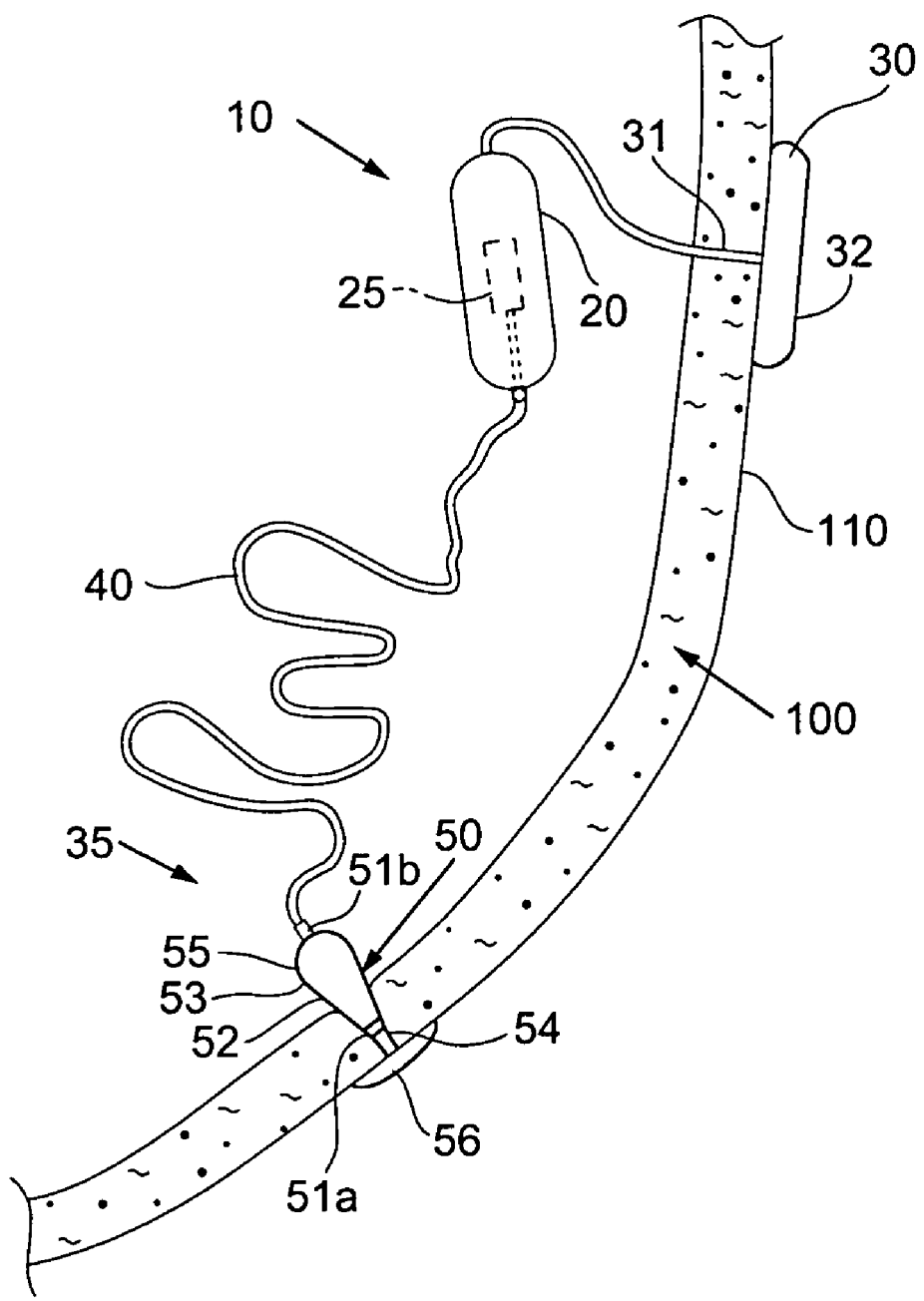
FIG. 1 is a schematic side view of a stimulator in accordance with the invention, implanted in a stomach.

Referring to FIG. 1, a stimulator 10 in accordance with the invention is illustrated attached to a stomach wall 100. The stimulator 10 comprises a housing 20 containing electronic circuitry 25. The stimulator 10 is attached with anchor 30 to the stomach wall 100. The anchor 30 comprises an elongate member 31 having an expandable distal anchor portion 32. The expandable distal anchor portion 32 may be deployed from the inside to the outside of the stomach wall where the expandable distal anchor portion 32 is expanded to engage to the outer surface 110 of the stomach wall 100. The elongate member 31 extends through the stomach wall between the expandable distal portion and the housing containing the electronic circuitry 25. An example of the deployment of an expandable member such as the expandable distal portion 32 is described, for example, in U.S. Pat. No. 6,535,764. The expandable distal anchor portion 32 may comprise, for example, a shape memory alloy, a spring member, or an inflatable member. The electronic circuitry is sealed in the housing 20.

The electronic circuitry 25 provides sensing, stimulating electronic pulses through electrodes to the stomach wall, and telemetry communication with an external unit such as a programmer, reader, recorder or controller. The outer shell of the housing is constructed of an acid corrosion resistant material such as a suitable inert polymer or an acid corrosion resistant metal such as Platinum, Gold, Tantalum, Titanium, or suitable alloys thereof.

The stimulator 10 further comprises a lead 35 in accordance with the invention. The lead 35 is coupled to the electronic circuitry 25 of the housing 20 with a flexible lead wire 40. The lead 35 extends out of the housing 20 and is positioned through the stomach wall with at least one electrode in contact with the tissue of the stomach.

The lead 35 comprises a retaining portion 50 including an elongate portion 52 that when deployed extends through the stomach wall 100. The elongate portion comprises a tapered portion 53 that when deployed extends at least in part through the stomach wall 100. The retaining portion 50 further comprises an expandable distal anchor portion 56 that may be deployed from the inside to the outside of the stomach wall in a manner similar to expandable distal portion 32. The expandable distal anchor portion 56 is expanded at the outside surface of the stomach and is configured to engage the outer surface 110 of the stomach wall. The expandable distal anchor portion acts as a stop to prevent the retaining portion 50 from pulling out and into the stomach. The elongate portion 52 extends at least in part through the stomach wall 100 and between the expandable distal anchor portion 56 and the housing 20.

The tapered portion 53 of the elongate portion 52 comprises a narrower portion 54 located outwardly towards the outside of the stomach with respect to a wider portion 55 which is more inward. The tapered portion 53 tapers from the wider portion 55 outwardly towards the narrower portion 54. The retaining portion 50 further comprises a first electrode 51a and a second 51b electrode, each electrode formed of a corrosion resistant metal conductor such as Platinum, Gold, Tantalum, Titanium or suitable alloys thereof. The first electrode 51a comprises a small ring electrode positioned on the narrower portion 54 and in electrical contact with the stomach wall 100. The electrode 51a may also be a partial ring of another configuration. The second electrode 5ib is located proximally of the first electrode 51b near the wider portion 55 of the elongate member 53. The electrodes 51a, 51b are coupled to conductors extending through flexible lead wire 40 which are coupled to the electronic circuitry 25.

The second electrode 51b has a much greater surface area than the first electrode 51a thus focusing the current density between the electrodes, with a higher current density at the first electrode 51a. The second electrode 51b is shown positioned adjacent the mucosa of the stomach. The larger surface area of the second electrode 5ib also provides a lower impedance, which compensates at least in part for the high impedance of the mucosa.

In a stimulator according to the invention and in use in a stomach, the second electrode 51b which is larger and more proximal may have a surface area between about 50 to 200 $mm^2$. The first electrode which is smaller and more distal may have a surface area between about 2 to 20 $mm^2$. The ratio of smaller to larger electrode area according to the invention may be between 1:40 and 2:5.

The tapered portion 53 of the elongate member 52 of FIG. 1 in combination with the expandable anchor portion 56 act to reduce movement of the retaining portion 50 with respect to the stomach wall 100 during stomach contractile behavior. Thus, the retaining portion 50 assists in maintaining electrical contact of the electrode 51a with the stomach wall. The anchor accordingly acts to reduce movement of the anchor and thus to maintain electrode contact with the stomach wall.

The circuitry 25 comprises, a microprocessor or controller for controlling the operations of the electronic circuitry 25, an internal clock, and device configured to power the various components of the circuit 25. The controller controls electrical stimulation delivered to stimulating electrodes 51, 52 in accordance with programmed parameters.

Figure 2A:
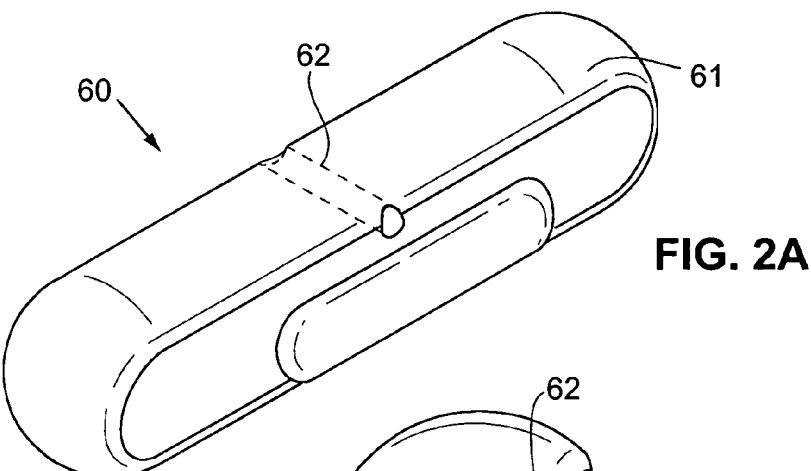
FIGS. 2A-2C are perspective views of a stimulator in accordance with the invention, implanted in a stomach.
Figure 2B:
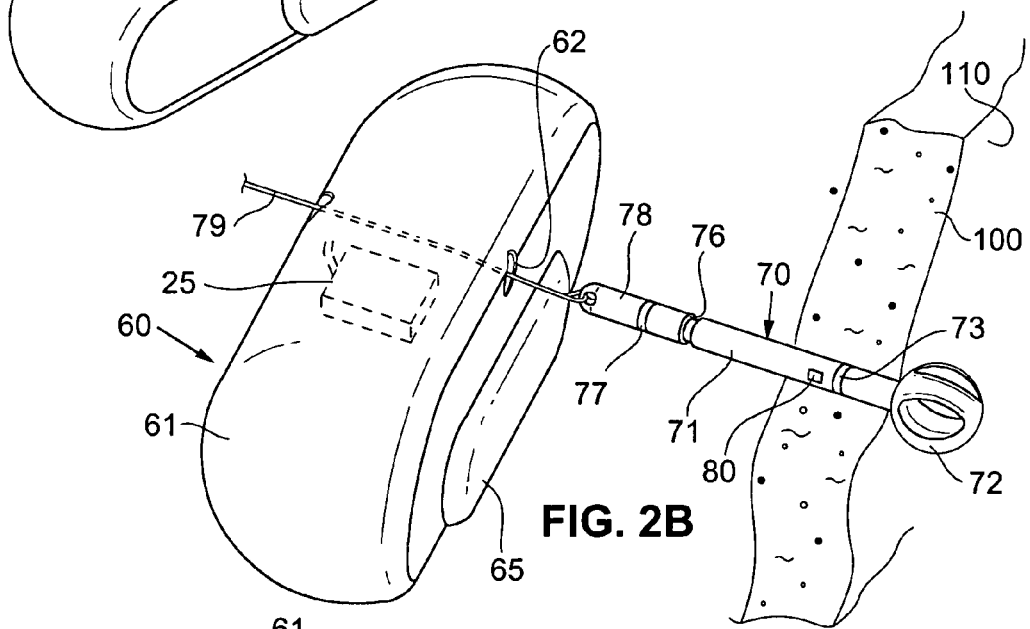
Figure 2C:
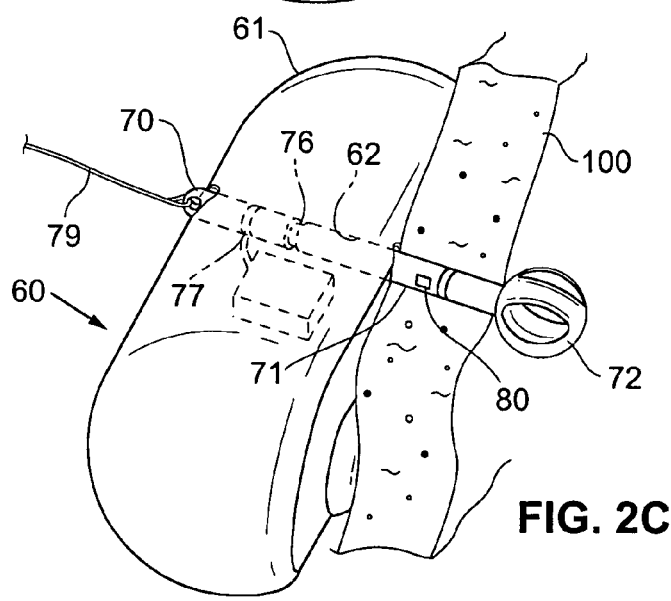

Referring to FIGS. 2A-2C, a stimulator 60 in accordance with the invention is illustrated. The stimulator 60 comprises an anchor 70 and a housing 61. The anchor 70 comprises an elongate member 71 having and expandable distal end 72. The housing 61 includes electronic circuitry 25 for supplying electrically stimulating signals through electrodes 65, 73 to the stomach wall tissue. The housing 61 further includes an opening 62 for receiving the elongate member 71 of the anchor 70 to removably couple the anchor 70 to the housing 60. A notch 76 in the elongate member 71 engages a catch in the opening 62 of the housing 61 to couple the anchor 70 to the housing 61.

As illustrated in FIG. 2B, the anchor 70 is positioned through the stomach wall 100 and the expandable distal end 72 is expanded to anchor the anchor 70 on the stomach wall. The anchor 70 includes an electrode 73 positioned on the elongate member 71 so that when the anchor 70 is deployed, it is in electrical contact with the stomach wall 100. The anchor 70 further includes an electrical contact that extends from the electrode 73 through the elongate member 71 to an external contact 77 on the elongate member 71 that couples with a contact within the opening 62 in the housing 61 to electrically couple the electrode to electronic circuitry 25 contained within the housing 61.

The housing 61 further contains a large area electrode 65. Electrode 73 on the anchor 70 and electrode 65 on the housing 61 form an electrode pair. The electrode 73 is a relatively smaller area electrode in comparison to electrode 65. According to one example of the invention in use in a stomach, the electrode 65 which is larger and more proximal may have a surface area between about 50 to 200 mm$^2$. The electrode 73 which is smaller and more distal may have a surface area between about 2 to 20 mm$^2$. The ratio of smaller to larger electrode area may be between 1:40 and 2:5.

The electrodes 65, 73 are formed of a corrosion resistant metal conductor such as Platinum, Gold, Tantalum, Titanium or suitable alloys thereof.

A tether 79 is secured to the proximal end 78 of the elongate member 71. The tether 79 is used to guide the opening 62 of the housing 61 into place over the elongate member 71 of the anchor 70 which is anchored to the stomach wall 100 (See FIG. 2B).

A sensor 80 for sensing various parameters of the stomach is located on the elongate member 71 of the anchor 70.

The sensor 80 is coupled through a conductor (not shown) to an electrical contact on the elongate member 73 so that when the housing 61 is coupled to the anchor 70, the sensor is in communication with the electronic circuitry in the housing 61 through an electrical contact in the opening 62 of the housing 61. A variety of different sensors may be used to sense parameters or conditions of the stomach or patient. For example, a sensor may be a mechanical sensor that senses stomach wall contractions. Alternatively, electrical sensors may detect changes in impedance due to changes in wall thickness from smooth muscle contractions. Other examples of such sensors may include, for example, pH sensors, impedance sensors, pressure sensors and temperature measuring devices.

Figure 3:
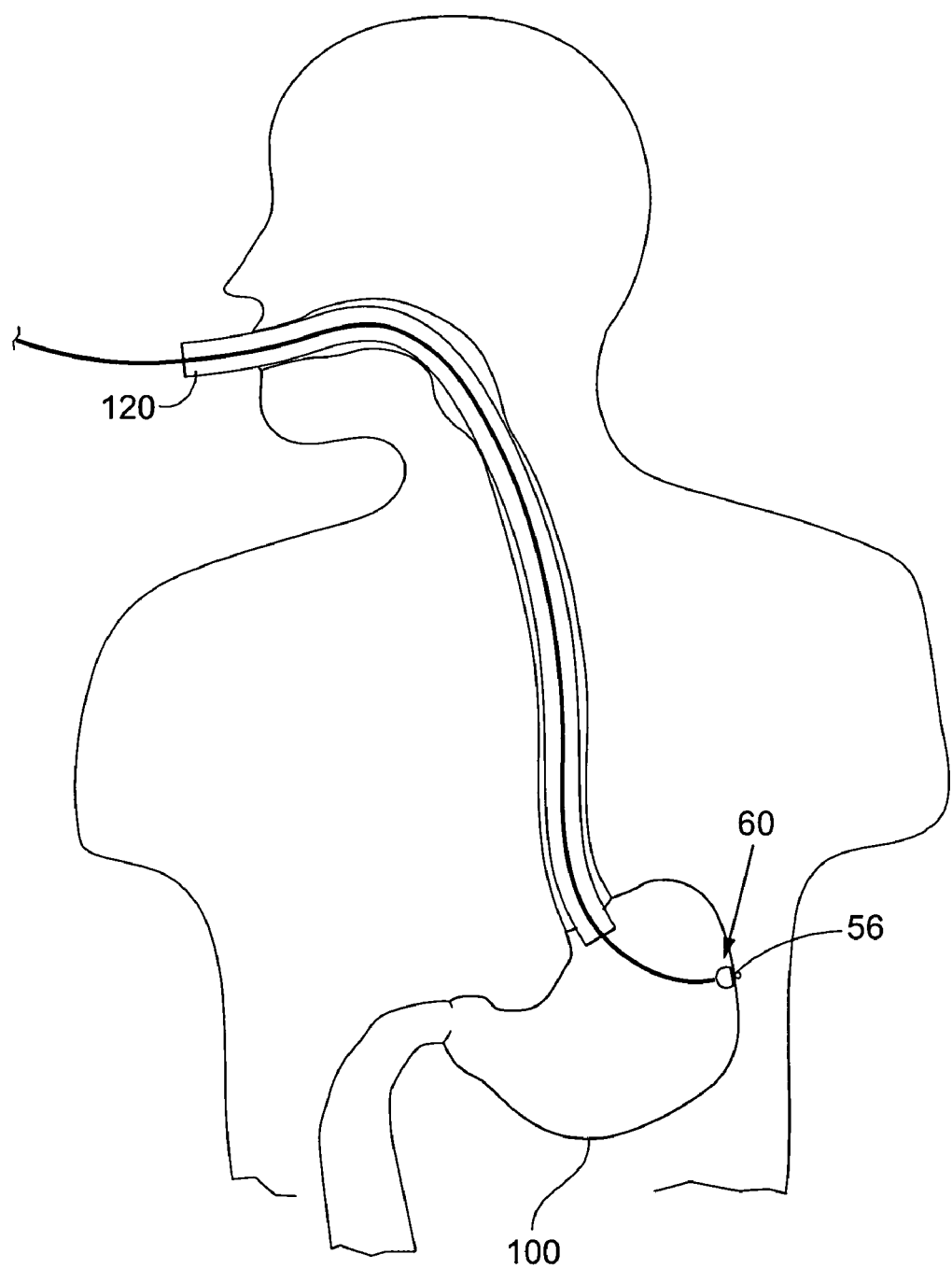
FIG. 3 is a schematic view of a stimulator being endoscopically implanted in a stomach.

FIG. 3 illustrates the placement of a stimulator in accordance with the invention in the stomach an endoscope of the system of the present invention a flexible endoscope 120 is used to locate an attachment site in the stomach 100 and attach the stimulator device to the stomach wall of a patient. The flexible endoscope 120 is of the type that is typically used by gastroenterologists in accessing the esophagus or stomach. The endoscope allows the physician to visualize while performing procedures on the upper gastrointestinal tract. The flexible endoscope may be, for example, a flexible fiber optic endoscope utilizing optic fibers for imaging or a video endoscope that uses a CCD (charge coupled device) to provide video images. Such endoscopes typically include a fiber optic light guide and a complex objective lens at the distal end to focus the image.

Memory devices located in the electronic circuitry (or alternatively in an external device in communication with the electronic circuitry) contain the program instructions for the controller and any other permanently stored information that allows the controller to operate. The memory devices may also contain programmable memory. A telemetry coil or other communication device that communicates with an external control or programming device may also be provided. Thus information may be downloaded or uploaded from or to an external device. The circuit 25 may also be coupled to one or more sensors.

The stimulation modes and parameters can either be set using the external programmer, or they may be set in response to sensory feedback.

The electronic circuitry 25 may communicate with an external device that may be capable of receiving, displaying, or analyzing data from the electronic circuitry and also may be capable of programming, controlling or other communications with the electronic circuitry 25. The electronic circuitry 25 may also comprises a passive device that may be powered and controlled by an external device.

The materials of the attachment devices, stimulators and housings of the present invention are preferably selected for long-term use in the stomach, i.e., two or more years. Suitable materials include the materials described herein.

While the invention has been described with reference to preferred embodiments and in particular to a gastric stimulator, the present invention contemplates that the attachment devices may be used to attach a number of functional devices to the wall of digestive organs.

While the invention has been described with reference to certain embodiments, it will be understood that variations and modifications may be made within the scope of the following claims. Such modifications may include substituting elements or components which perform substantially the same function in substantially the same way to achieve substantially the same result that the invention can be practiced with modification within the scope of the following claims.

What is claimed is:

1. An implantable stimulator for stimulating a digestive organ comprising:
   a first implantable pseudounipolar electrode configured to be positioned in electrical contact with the digestive organ when deployed, wherein the first electrode has a first surface area in the range of about 2 mm$^2$ to about 20 mm$^2$;
   a second implantable electrode configured to engage tissue of the digestive organ and disposed so as to form an electrode pair with the first electrode when deployed, wherein the second electrode has a second surface area in the range of about 50 mm$^2$ to about 200 mm$^2$; and
   a retention device including said first electrode, the retention device in use, attaching to a wall of the organ so as to reduce movement of the retention device and maintain electrode contact between the deployed first electrode and the wall of the organ when the stimulator is implanted, so that the surface of the first electrode remains in electrical contact with the digestive organ during long-term implantation of the stimulator and long-term stimulation of the organ.

2. The stimulator of claim 1 wherein the ratio of the first surface area to the second surface area is about 2:5 or less.

3. The stimulator of claim 2 wherein the ratio of the first surface area to the second surface area is between about 1:40 and 2:5.

4. The stimulator of claim 1 wherein the second electrode is located on the retention device.

5. The stimulator of claim 1 further comprising electronic circuitry configured to be coupled to the first electrode and second electrode to deliver an electrical signal to the digestive organ.

6. The stimulator of claim 5 wherein the electronic circuitry is disposed within an electronics housing and the second electrode is located on the housing.

7. The stimulator of claim 1 wherein the implantable stimulator is configured to be delivered endoscopically to the digestive organ.

8. The stimulator of claim 1 wherein the implantable stimulator is configured to be attached to a stomach wall.

9. The stimulator of claim 1 further comprising an anchor, the anchor having:
   an expansible distal portion and an elongate portion coupled to the expansible distal portion wherein the elongate portion is configured to extend through the wall of the digestive organ when deployed, the elongate portion comprising a narrower more distal portion and wider more proximal portion; and wherein the first electrode is located on the narrower more distal portion of the elongate member, and wherein the second electrode is located on the wider more proximal portion of the elongate member.

10. A stimulator for stimulating a digestive organ comprising:
an implantable stimulator comprising:
an implantable power source;
a first pseudounipolar electrode having a first surface area and configured to be positioned in electrical contact with the digestive organ when deployed;
a second electrode having a second surface area and configured to engage tissue of the digestive organ when deployed so as to form an electrode pair with the first electrode when deployed, the first and second electrodes coupled to the power source; and
a retention device including said first electrode, the retention device having opposed surfaces that, in use, attach to a wall of the organ so as to reduce movement of the retention device and maintain electrode contact between the deployed first electrode and the wall of the organ, and wherein the ratio of the first surface area to the second surface area is about 2:5 or less during long-term implantation of the stimulator and long-term stimulation of the digestive organ.

11. The stimulator of claim 10 wherein the second electrode is located on the retention device.

12. The stimulator of claim 10 further comprising electronic circuitry configured to be coupled to the first electrode and second electrode to deliver an electrical signal to the digestive organ.

13. The stimulator of claim 12 wherein the electronic circuitry is disposed within an electronics housing and the second electrode is located on the housing.

14. The stimulator of claim 10 wherein the stimulator is configured to be delivered endoscopically to the digestive organ.

15. The stimulator of claim 10 wherein the stimulator is configured to be attached to a stomach wall.

16. The stimulator of claim 10 further comprising an anchor, the anchor having:
an expansible distal portion and an elongate portion coupled to the expansible distal portion wherein the elongate portion is configured to extend through the wall of the digestive organ when deployed, the elongate portion comprising a narrower more distal portion and wider more proximal portion wherein the first electrode is located on the narrower more distal portion of the elongate member, and wherein the second electrode is located on the wider more proximal portion of the elongate member.

* * * * *